(12) United States Patent
Ford

(10) Patent No.: US 9,409,863 B2
(45) Date of Patent: Aug. 9, 2016

(54) PROCESS FOR PREPARING CHLOROAMINES

(71) Applicant: BAYER INTELLECTUAL PROPERTY GMBH, Monheim (DE)

(72) Inventor: Mark James Ford, Schmitten (DE)

(73) Assignee: BAYER INTELLECTUAL PROPERTY GMBH, Monheim am Rhein (DE)

(*) Notice: Subject to any disclaimer, the term of this patent is extended or adjusted under 35 U.S.C. 154(b) by 0 days.

(21) Appl. No.: 14/379,133

(22) PCT Filed: Feb. 13, 2013

(86) PCT No.: PCT/EP2013/052826
§ 371 (c)(1),
(2) Date: Aug. 15, 2014

(87) PCT Pub. No.: WO2013/012874
PCT Pub. Date: Aug. 22, 2013

(65) Prior Publication Data
US 2015/0025245 A1 Jan. 22, 2015

(30) Foreign Application Priority Data
Feb. 17, 2012 (EP) ..................................... 12155970

(51) Int. Cl.
*C07D 211/92* (2006.01)
*C07C 239/04* (2006.01)

(52) U.S. Cl.
CPC ............ *C07D 211/92* (2013.01); *C07C 239/04* (2013.01)

(58) Field of Classification Search
CPC ............................. C07D 211/92; C07D 239/04
USPC ......................................................... 546/186
See application file for complete search history.

(56) References Cited

FOREIGN PATENT DOCUMENTS

JP 47-25178 * 10/1972

OTHER PUBLICATIONS

Hall "The effect of axial ... " Journal of Organic Chemistry 29(11), 3135-8 (1964).*
Murayama et al. "N-halocycloalkanes ... " CA78:4130 (1973).*
Ingold et al. "Kinetic Application of ... " J. Am. Chem. Soci. 95(19) 6400-6404 (1973).*
Toshimasa et al. "Studies on stable ... "Bull. Chem. Soc. Japan, v.45, p. 1802-1806 (1972).*
PCT-237*
International Search Report received in corresponding PCT/EP2013/052826, mailed Apr. 19, 2013.
Oscar Bally, Einwirkung von Chlor auf Pyridin. Pi peri din and Derivate derselben 11, Chem Sche Berichte, vol. 21. 1888. pages 1772-1777. XP002694687.
Toshimasa Toda et al: 11 Studies on Stable Free Radicals. X. Photolysis of Hindered N-Chloroamines 11, Bulletin of the Chemical Society of Japan, vol. 1, 45. No. 6.Jan. 1, 1972. pp. 1802-1806. XP055058175.
D. Matte et al.: 11 Etude cinetique de la N-chloration de la dimethylamine et de la diethylamine en phase aqueuse 11, Canadian Journal of Chemistry, vol. 67. 1989. pp. 786-791. XP002694688.
Jerzy Zakrzewski: 11 a Simple Method for the Synthesis of the Sterically Hindered Chloramines 11, Synthetic Communications: An International, Journal for Rapid Communication of Synthetic Organic Chemistry. Taylor & Francis Inc. Philadelphia. PA; US, vol. 18., No. 16-17. Jan. 1, 1988, pp. 2135-2140. XP008152354.
Favreau, et al., "Novel synthesis of 3-oxazolines", Tetrahedron Letters 41 (2000) 9787-9790.
Kovacic, et al., "Chemistry of N-Bromamines and N-Chloramines", Chemical Reviews, 1970, vol. 70, No. 6, Oct. 3, 1968, pp. 639-664.
Malatesta, et al., "Kinetic Applications of Electron Paramagnetic Resonance Spectroscopy. XL. Aminium Radicals", Journal of the American Chemical Society / 95:19 / Sep. 19, 1973, pp. 6400-6404.
Snider, et al. "Synthesis of (()-Cylindricines A, D, and E", J. Org. Chem. 1997, 62, 5630-5633.
Spanswick et al., "Halogenation with N-haloamines in strong acids. I. The nature of the chain propagating radical", Division of Chemistry, National Research Council of Canada, Ottawa, Canada, Received Sep. 8, 1969, pp. 547-553.

* cited by examiner

*Primary Examiner* — Celia Chang
(74) *Attorney, Agent, or Firm* — McBee Moore Woodward Vanik IP, LLC

(57) ABSTRACT

The present application relates to a process for preparing chloroamines which can be used as precursors for syntheses of fine chemicals and active ingredients from pharmaceuticals and/or agriculture, by reaction of secondary amines of the formula (II) with chlorine gas in the presence of an aqueous alkali metal or alkaline earth metal oxide base.

10 Claims, No Drawings

PROCESS FOR PREPARING CHLOROAMINES

CROSS REFERENCE TO RELATED APPLICATIONS

This application is a §371 National Stage Application of PCT/EP2013/052826, filed Feb. 13, 2013, which claims priority to EP 12155970.2, filed Feb. 17, 2012.

BACKGROUND

1. Field of the Invention

The present application relates to a process for preparing chloroamines of the formula (I) which can be used as precursors for syntheses of fine chemicals and active ingredients from pharmaceuticals and/or agriculture (Kovacic et al. Chemical Reviews 1970, 70, 6, 639).

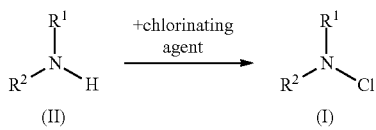

It is known that, in secondary amines (II) where $R^1$ and $R^2$ are each independently selected from alkyl radicals or, together with the nitrogen atom to which they are bonded, may form a 5- or 6-membered ring, hydrogen can be exchanged for chlorine with a chlorinating agent.

2. Description of Related Art

In the case of sterically hindered secondary amines, very active N-chloroamides, for example N-chlorosuccinimide (Kovacic et al., Chemical Reviews 1970, 70, 6, 639) or sodium dichloroisocyanurate (Zakrzewski, Synthetic Communications 1988, 18 (16&17), 2135), are required as chlorinating agents. However, the yields are usually only moderate (75-86%) and, even when the yields are better (e.g.: J. Org. Chem. 1997, 62, 16, 5631), one equivalent of the amide is unavoidably obtained as waste, which is both economically and ecologically disadvantageous. The direct chlorination of 2,2,6,6-tetramethylpiperidine with sodium hypochlorite solution (commonly known as bleach or liquid bleach) is known (Ingold et al., JACS, 1973, 6400). The yield is only 77% and the dilutions of 100 ml of liquid bleach per 7 g of amine used in the reaction described lead to low space-time yields in an industrial process. A better yield (96.5%) was described by Toshimasa et al., Bull. Chem. Soc. Jap., 1972, 45, 1802. Here, however, for 28 g of 2,2,6,6-tetramethylpiperidine, 220 ml of aqueous HCl and 250 ml of liquid bleach were actually consumed. Such a great salt load is also disadvantageous in industry, and forms as a result of an excess of chlorinating agent which has to be degraded on the industrial scale at the end of the reaction. The formation, reported in Bull. Chem. Soc. Jap., 1972, 45, 1802, of 1-chloro-2,2,5,5-tetramethyl-4-oxoimidazolidine with 94% yield is described only with an excess of chlorinating agent and in the case of dilutions of 1.4 g of amine in 40 ml of liquid bleach. Fellous et al., Tetrahedron Lett., 2000, 9787, in the case of such chlorinations describe only yields of 76-91% according to the substrate. The 10 equivalents (eq.) of the chlorinating agent used also show that the synthesis of N-chlorodialkylamines on the industrially relevant scale remains an unsolved problem.

Inevitably, in the case of use of liquid bleach (NaOCl), at least one equivalent of additional salt is obtained (Scheme 1), often with formation of more than 2 equivalents thereof. For example, Bull. Soc. Chem. Jap. describes the formation of 2.66 equivalents of salt in order to fully scavenge the chlorine. Since the pH rises at the end of the reaction (as a result of formation of NaOH), the oxidation potential of the liquid bleach falls in the course of the reaction. This explains the incomplete reaction even if greater excesses of liquid bleach are used.

Scheme 1:

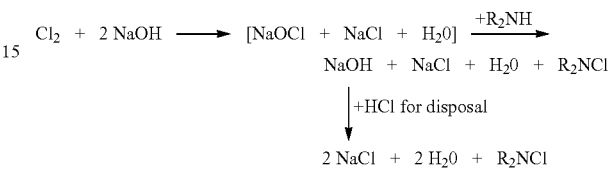

Spanswick et. al., Can. J. Chem., 1970, 48, 548 state that chloroamines in the presence of strong acids are themselves good chlorinating agents. Consequently, the scavenging of HCl formed is essential.

It is thus an object of the present invention to provide a process for preparing sterically hindered chloroamines which overcomes the above-described disadvantages.

The object was achieved by a process for preparing chloroamines of the formula (I)

wherein $R^1$ and $R^2$ are each independently selected from the group consisting of $(C_1-C_8)$alkyl optionally substituted by 1-2 $R^3$ radicals;
or
$R^1$ and $R^2$ together form a —$(CH_2)_4$—, —$(CH_2)_5$— or —$(CH_2)_2O(CH_2)_2$— group, where each of these groups may optionally be substituted by 1-4 $R^4$ radicals;
$R^3$ are each independently selected from halogen, $(C_1-C_3)$alkoxy, $(C_1-C_3)$haloalkoxy, $(C_1-C_3)$alkylamino, $(C_2-C_4)$dialkylamino and $(C_2-C_4)$alkoxycarbonyl;
$R^4$ is selected from halogen, $(C_1-C_3)$alkyl, $(C_1-C_3)$alkoxy, $(C_1-C_3)$haloalkoxy, $(C_1-C_3)$alkylamino, $(C_2-C_4)$dialkylamino and $(C_2-C_4)$alkoxycarbonyl,
by reaction of secondary amines of the formula (II)

in which the $R^1$ and $R^2$ radicals are each as defined above with chlorine gas in the presence of an aqueous alkali metal or alkaline earth metal oxide base.

DETAILED DESCRIPTION OF A PREFERRED EMBODIMENT

In a preferred embodiment of the invention,
$R^1$ and $R^2$ together form a —$(CH_2)_4$—, —$(CH_2)_5$— or —$(CH_2)_2O(CH_2)_2$— group, where each of these groups may optionally be substituted by 1, 2, 3 or 4 $R^5$ radicals, and
$R^5$ is selected from methyl, ethyl, n-propyl and i-propyl.

In a particularly preferred embodiment of the invention, $R^1$ and $R^2$ together form a —$(CH_2)_5$— group substituted by 4 methyl groups.

In the context of the present invention, 2,2,6,6-tetramethylpiperidine is used as a very particularly preferred secondary amine of the formula (II).

The term "halogen" or "halogen atom" means, for example, fluorine, chlorine, bromine or iodine. When the term is used for a radical, "halogen" or "halogen atom" means, for example, a fluorine, chlorine, bromine or iodine atom.

Alkyl means a straight-chain, branched or cyclic hydrocarbyl radical. The expression "$(C_1-C_4)$-alkyl", for example, is a brief notation for alkyl having one to 4 carbon atoms according to the range stated for carbon atoms and encompasses, for example, the methyl, ethyl, 1-propyl, 2-propyl, 1-butyl, 2-butyl, 2-methylpropyl, tert-butyl, cyclopropyl and cyclobutyl radicals. General alkyl radicals with a larger specified range of carbon atoms,
e.g. "$(C_1-C_6)$alkyl", correspondingly also encompass straight-chain, branched or cyclic alkyl radicals with a greater number of carbon atoms, i.e. according to the example also the alkyl radicals having 5 and 6 carbon atoms.

Unless stated specifically, for the hydrocarbyl radicals such as alkyl, alkenyl and alkynyl radicals, including in composite radicals, preference is given to the lower carbon skeletons, for example having 1 to 6 carbon atoms, or having 2 to 6 carbon atoms in the case of unsaturated groups. Alkyl radicals, including in the composite radicals such as alkoxy, haloalkyl etc., mean, for example, methyl, ethyl, cyclo-, n- or i-propyl, cyclo-, n-, t- or 2-butyl, pentyls, hexyls such as cyclohexyl, n-hexyl, i-hexyl and 1,3-dimethylbutyl, heptyls such as cycloheptyl, n-heptyl, 1-methylhexyl and 1,4-dimethylpentyl.

Preferred cyclic alkyl radicals preferably have 3-8 ring carbon atoms, for example cyclopropyl, cyclobutyl, cyclopentyl or cyclohexyl. In the case of optionally substituted cyclic alkyl radicals, cyclic systems with substituents are included, also including substituents with a double bond on the cyclic alkyl radical, for example an alkylidene group such as methylidene.

In the case of optionally substituted cyclic alkyl radicals, polycyclic aliphatic systems are also included, such as bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), adamantan-1-yl and adamantan-2-yl.

In the case of optionally substituted cyclic alkyl radicals, spirocyclic aliphatic systems are also included, for example spiro[2.2]pent-1-yl, spiro[2.3]hex-1-yl, spiro[2.3]hex-4-yl, 3-spiro[2.3]hex-5-yl.

Aryl is a mono-, bi- or polycyclic aromatic system having preferably 6 to 14, especially 6 to 10, ring carbon atoms, for example phenyl, indanyl, naphthyl, anthryl, phenanthrenyl and the like, preferably phenyl.

When two or more radicals form one or more rings, these may be carbocyclic, heterocyclic, saturated, partly saturated, unsaturated, for example also aromatic and optionally further substituted. The fused rings are preferably 5- or 6-membered rings, particular preference being given to benzofused cycles.

The substituents mentioned by way of example ("first substituent level") may, if they contain hydrocarbonaceous moieties, optionally be further substituted therein ("second substituent level"), for example by one of the substituents as defined for the first substituent level. Corresponding further substituent levels are possible. The term "substituted radical" preferably embraces just one or two substituent levels.

Preferred substituents for the substituent levels are, for example,
halogen, nitro, cyano, isocyano, carboxyl, carbonamide, $SF_5$, alkyl, monoalkylamino, dialkylamino, N-alkanoylamino, alkoxy, alkoxycarbonyl, aryloxycarbonyl, alkanoyl, arylcarbonyl, alkylsulphinyl, including both enantiomers of the alkylsulphinyl group, alkylsulphonyl, monoalkylaminosulphonyl, dialkylaminosulphonyl, alkylphosphinyl, alkylphosphonyl, including both enantiomers for alkylphosphinyl and alkylphosphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, arylamino, benzylamino, heterocyclyl and trialkylsilyl.

Substituents composed of more than one substituent level are preferably, for example, alkoxyalkyl such as monoalkoxyalkyl or dialkoxyalkyl, alkoxyalkoxy such as monoalkoxyalkoxy or dialkoxyalkoxy, benzyl, phenethyl, benzyloxy, haloalkyl, haloalkoxy, haloalkanoyl, haloalkylcarbonyl, haloalkoxycarbonyl, haloalkoxyalkoxy, haloalkoxyalkanoyl, haloalkoxyalkyl, alkanoylalkyl, haloalkanoylalkyl, alkanoyloxyalkyl.

In the case of radicals having carbon atoms, preference is given to those having 1 to 6 carbon atoms, preferably 1 to 4 carbon atoms, especially 1 or 2 carbon atoms. Preference is generally given to substituents from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Particular preference is given here to the substituents methyl, methoxy, fluorine and chlorine.

Substituted amino such as mono- or disubstituted amino is a radical from the group of the substituted amino radicals which are N-substituted, for example, by one or two identical or different radicals from the group of alkyl, hydroxyl, amino, alkoxy, acyl and aryl; preferably mono- and dialkylamino, mono- and diarylamino, such as optionally substituted anilines, acylamino, N,N-diacylamino, N-alkyl-N-arylamino, N-alkyl-N-acylamino and saturated N-heterocycles; preference is given to alkyl radicals having 1 to 4 carbon atoms; aryl is preferably phenyl or substituted phenyl; the definition given below applies to acyl, preferably $(C_1-C_4)$ alkanoyl. The same applies to substituted hydroxylamino or hydrazino.

Substituted amino also includes quaternary ammonium compounds (salts) with four organic substituents on the nitrogen atom.

A group equivalent to the carboxyl group is, for example, an alkyl ester, aryl ester, carboximide ester, 5,6-dihydro-1,2,4-dioxazin-3-yl; 5,6-dihydro-1,2,4-oxathiazin-3-yl, trialkyl orthoester, dialkoxyalkylamino ester, dialkylaminoalkoxy ester, trialkylamino ester, amidines, dialkoxyketene acetals.

Optionally substituted phenyl is preferably phenyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$ haloalkoxy, cyano, isocyano and nitro, e.g. o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted heterocyclyl is preferably heterocyclyl which is unsubstituted or mono- or polysubstituted, preferably up to trisubstituted, by identical or different radicals from the group of halogen, cyano, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-$ $C_4$)alkyl, ($C_1$-$C_4$)haloalkyl, ($C_1$-$C_4$)haloalkoxy, nitro and oxo, and is especially mono- or polysubstituted by radicals from the group of halogen, ($C_1$-$C_4$)alkyl, ($C_1$-$C_4$)alkoxy, ($C_1$-$C_4$)haloalkyl and oxo, very particularly by one or two ($C_1$-$C_4$)alkyl radicals.

Haloalkyl is alkyl partly or fully substituted by identical or different halogen atoms, for example monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2CHFCl$, $CHCl_2$, $CF_2CF_2H$, $CH_2CF_3$; haloalkoxy is, for example, $OCF_3$, $OCHF_2$, $OCH_2F$, $OCF_2CF_3$, $OCH_2CF_3$ and $OCH_2CH_2Cl$; the same applies to haloalkenyl and other halogen-substituted radicals.

It has been found that, surprisingly, a mixture of a secondary amine, for example 2,2,6,6-tetramethylpiperidine, and one equivalent of concentrated hydroxide base can be converted directly to the corresponding N-chloro derivative in virtually quantitative yield at low temperatures and with a small excess of chlorine gas.

The inventive direct utilization of chlorine in the presence of only one equivalent of hydroxide for scavenging of HCl formed is shown in Scheme 2 below.

Scheme 2:

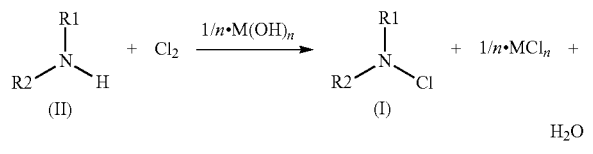

$H_2O$

Based on the amine of the formula (II), according to the present invention, 1.0 to 1.5 base equivalents (n=number of hydroxyl groups), preferably 1.0 to 1.2 base equivalents, of the alkali metal or alkaline earth metal hydroxide base are used. Particular preference is given to using the base in an equimolar ratio. In the case of alkaline earth metal hydroxides (Scheme 2, n=2), for example $Ca(OH)_2$, correspondingly only 0.5 to 0.75 equivalent, preferably 0.5 to 0.6 equivalent, more preferably 0.5 to 0.55 equivalent, is used.

The chlorine gas used for chlorination is used in a small excess of 1.1 to 1.5 equivalents, preferably 1.1 to 1.3 equivalents, more preferably 1.1 to 1.2 equivalents, of $Cl_2$, based on the amine of the formula (II) to be chlorinated.

Suitable alkaline earth metal bases (n=2) are selected from the group consisting of magnesium hydroxide and calcium hydroxide.

Suitable alkali metal bases (n=1) are selected from the group consisting of lithium hydroxide, sodium hydroxide and potassium hydroxide.

The inventive chlorination is performed within a temperature range from +20 to −15° C., preferably +10 to −10° C., more preferably +5 to −5° C.

The concentration of the aqueous base used is preferably selected such that it has a maximum concentration, but the chloride salt formed is fully dissolved at the workup temperature.

As soon as the reaction has ended, the aqueous salt phase, possibly after heating to room temperature or temperatures, for example, below 50° C., can be separated easily from the N-chloroamine.

Compared to the processes described in the prior art, the process according to the invention, owing to the higher concentrations, can achieve a much higher space-time yield.

For workup of the reaction mixture, the aqueous phase can optionally be washed with an unreactive organic solvent and added to the main fraction. Suitable organic solvents are, for example, selected from the group consisting of alkanes, e.g.: heptane; haloalkanes, e.g.: dichloromethane, dichloroethane; aromatics, e.g.: toluene, xylene, ethylbenzene, chlorobenzene, benzotrifluoride; cycloalkanes, e.g.: cyclohexane and methylcyclohexane; esters, e.g.: ethyl acetate, butyl acetate, isopropyl acetate.

If this solvent forms an azeotrope with water, the distillative recovery of the solvent simultaneously can also serve to dry the N-chloroamine. Suitable solvents which form an azeotrope with water are, for example, selected from the group consisting of toluene and xylene.

The present invention is to be illustrated in detail by the examples which follow.

EXAMPLES

Example 1

Use of NaOH as a Base 20 g of 2,2,6,6-tetramethylpiperidine are mixed with 40.7 g, 1.1 eq, of 15% sodium hydroxide solution and cooled to 5 to 10° C. Over a period of 1.5 hours, 10.8 g, 1.1 eq. of chlorine gas are introduced, then nitrogen gas is used to drive out the excess chlorine and the mixture is warmed to room temperature (RT). After separating the phases, washing the aqueous phase with 25 ml of dichloromethane, drying the combined organic phases with magnesium sulphate and distilling off the dichloromethane in vacuo, 24.2 g, 99%, of 1-chloro-2,2,6,6-tetramethylpiperidine are obtained.

Example 2

Use of $Ca(OH)_2$ as a Base 20 g of 2,2,6,6-tetramethylpiperidine are mixed with water and 6.42 g, 0.6 eq., of calcium hydroxide, and the suspension is cooled to 5° C. Over a period of 1.5 hours, 10.8 g, 1.1 eq. of chlorine gas are introduced, then nitrogen gas is used to drive out the excess chlorine and the mixture is warmed to RT. After separating the phases, washing the aqueous phase with 25 ml of dichloromethane, drying the combined organic phases with magnesium sulphate and distilling off the dichloromethane in vacuo, 24.2 g, 99%, of 1-chloro-2,2,6,6-tetramethylpiperidine are obtained.

Example 3

Use of NaOH as a Base 30 g of 2,2,6,6-tetramethylpiperidine are mixed with 61.1 g, 1.1 eq., of 15% sodium hydroxide solution and cooled to 5 to 10° C. Over a period of 1.2 hours, 16.2 g, 1.1 eq. of chlorine gas are introduced, then nitrogen gas is used to drive out the excess chlorine and the mixture is warmed to RT. After separating the phases and washing the aqueous phase with 15 ml of toluene, the organic phases are combined and the solvent is distilled off in vacuo, and 36.2 g, 99%, of 1-chloro-2,2,6,6-tetramethylpiperidine are obtained.

The invention claimed is:
1. Process for preparing a chloroamine of formula (I)

wherein
$R^1$ and $R^2$ together form a —$(CH_2)_5$— group substituted by 4 methyl groups;
by reaction of 2,2,6,6-tetramethylpiperidine,
with chlorine gas in the presence of an aqueous alkali metal or alkaline earth metal oxide base.

2. Process according to claim 1, wherein said process is executed within a temperature range from +10 to −10° C.

3. Process according to claim 1, wherein the alkali metal or alkaline earth metal oxide base, based on the base equivalents thereof, and the chlorine gas are used in equimolar amounts, or the base is used in a slight excess.

4. Process according to claim 1, wherein the alkaline earth metal base is selected from the group consisting of magnesium hydroxide and calcium hydroxide.

5. Process according to claim 1, wherein the alkali metal base is selected from the group consisting of lithium hydroxide, sodium hydroxide and potassium hydroxide.

6. Process according to claim 1, wherein the concentration of the aqueous alkali metal or alkaline earth metal oxide base is selected such that the alkali metal or alkaline earth metal chloride salts which form substantially dissolve below 50° C.

7. Process according to claim 1, further comprising the step of washing the aqueous phase with an unreactive organic solvent.

8. Process according to claim 7, wherein the unreactive organic solvent is selected from the group consisting of alkanes, haloalkanes, aromatics, cycloalkanes and esters.

9. Process according to claim 1, further comprising the step of separating the chloroamine of formula (I) from an aqueous salt phase.

10. Process according to claim 1, further comprising synthesizing a pharmaceutical or agricultural active ingredient from the chloroamine.

\* \* \* \* \*